(12) United States Patent
Ochiai et al.

(10) Patent No.: US 9,888,936 B2
(45) Date of Patent: Feb. 13, 2018

(54) DEVICE AND METHODS FOR USE DURING ARTHROSCOPIC SURGERY

(71) Applicant: SMITH & NEPHEW, INC., Memphis, TN (US)

(72) Inventors: Derek H. Ochiai, Great Falls, VA (US); Paul Alexander Torrie, Marblehead, MA (US)

(73) Assignee: Smith & Nephew, Inc., Memphis, TN (US)

( * ) Notice: Subject to any disclaimer, the term of this patent is extended or adjusted under 35 U.S.C. 154(b) by 3 days.

(21) Appl. No.: 14/947,346

(22) Filed: Nov. 20, 2015

(65) Prior Publication Data
US 2016/0228144 A1  Aug. 11, 2016

Related U.S. Application Data (62) Division of application No. 13/246,799, filed on Sep. 27, 2011, now Pat. No. 9,192,404.
(Continued)

(51) Int. Cl.
| A61B 17/32 | (2006.01) |
| A61B 17/3211 | (2006.01) |
| A61B 17/22 | (2006.01) |

(52) U.S. Cl.
CPC ... *A61B 17/320016* (2013.01); *A61B 17/3211* (2013.01); *A61B 2017/22038* (2013.01);
(Continued)

(58) Field of Classification Search
CPC ............ A61B 17/32; A61B 17/320016; A61B 17/3209; A61B 17/32093; A61B 17/3211; A61B 17/3213; A61B 17/8897; A61B 2017/320024; A61B 17/320056; A61B 17/32113; A61B 17/32116; A61B 17/00469; A61B 5/6581

See application file for complete search history.

(56) References Cited

U.S. PATENT DOCUMENTS

| 86,016 A | 1/1869 | Howell |
| 3,347,234 A | 10/1967 | Voss |

(Continued)

FOREIGN PATENT DOCUMENTS

| CN | 1069644 A | 3/1993 |
| CN | 1625370 A | 6/2005 |

(Continued)

OTHER PUBLICATIONS

Office Action from related Mexican Patent Application No. MX/a/2013/003496 dated Mar. 16, 2016.
(Continued)

*Primary Examiner* — Kevin T Truong
*Assistant Examiner* — Tracy Kamikawa
(74) *Attorney, Agent, or Firm* — Burns & Levinson LLP; Joseph M. Maraia (57) ABSTRACT

The present disclosure relates to a method of use during arthroscopic surgery. The method includes inserting a cannulated needle into a joint area of the body, inserting a guidewire through the needle, removing the needle, and inserting an arthroscopy knife into the joint area via the use of the guidewire. An arthroscopy knife and another method of its use is also disclosed.

18 Claims, 5 Drawing Sheets

Related U.S. Application Data (60) Provisional application No. 61/386,718, filed on Sep. 27, 2010.

(52) U.S. Cl.
CPC .............. *A61B 2017/22039* (2013.01); *A61B 2017/320052* (2013.01)

(56) References Cited

U.S. PATENT DOCUMENTS

| | | |
|---|---|---|
| 3,508,334 A | 4/1970 | Weissman |
| 3,604,487 A | 9/1971 | Gilbert |
| 3,867,932 A | 2/1975 | Huene |
| 4,039,266 A | 8/1977 | O'Connell |
| 4,159,716 A | 7/1979 | Borchers |
| 4,363,250 A | 12/1982 | Suga |
| 4,580,563 A | 4/1986 | Gross |
| 4,580,663 A | 4/1986 | Gross |
| 4,708,139 A | 11/1987 | Dunbar |
| 4,712,547 A | 12/1987 | Bonnet |
| 4,721,116 A | 1/1988 | Schintgen |
| 4,722,331 A | 2/1988 | Fox |
| 4,739,751 A | 4/1988 | Sapega et al. |
| 4,830,023 A | 5/1989 | de Toledo et al. |
| 4,896,663 A | 1/1990 | Vandewalls |
| 4,917,699 A | 4/1990 | Chervitz |
| 4,960,134 A | 10/1990 | Webster |
| 5,152,764 A | 10/1992 | Goble |
| 5,152,790 A | 10/1992 | Rosenberg et al. |
| 5,176,515 A | 1/1993 | Andrews |
| 5,197,971 A | 3/1993 | Bonutti |
| 5,207,753 A | 5/1993 | Badrinath |
| 5,231,989 A | 8/1993 | Middleman et al. |
| 5,250,055 A | 10/1993 | Moore et al. |
| RE34,502 E | 1/1994 | Webster, Jr. |
| 5,289,963 A | 3/1994 | McGarry et al. |
| 5,292,330 A | 3/1994 | Shutt |
| 5,320,626 A | 6/1994 | Schmieding |
| 5,345,937 A | 9/1994 | Middleman et al. |
| 5,356,064 A | 10/1994 | Green et al. |
| 5,364,002 A | 11/1994 | Green et al. |
| 5,366,479 A | 11/1994 | McGarry et al. |
| 5,409,490 A | 4/1995 | Ethridge |
| 5,458,602 A | 10/1995 | Goble et al. |
| 5,484,095 A | 1/1996 | Green et al. |
| 5,497,933 A | 3/1996 | DeFonzo et al. |
| 5,514,144 A | 5/1996 | Bolton |
| 5,520,693 A | 5/1996 | McGuire et al. |
| 5,545,175 A | 8/1996 | Abidin et al. |
| 5,549,617 A | 8/1996 | Green et al. |
| 5,562,664 A | 10/1996 | Durlacher |
| 5,562,689 A | 10/1996 | Green et al. |
| 5,573,538 A | 11/1996 | Laboureau |
| 5,575,801 A | 11/1996 | Habermeyer et al. |
| 5,584,839 A | 12/1996 | Gieringer |
| 5,601,550 A | 2/1997 | Esser |
| 5,609,596 A | 3/1997 | Pepper |
| 5,637,112 A | 6/1997 | Moore et al. |
| 5,643,273 A | 7/1997 | Clark |
| 5,643,294 A | 7/1997 | Tovey et al. |
| 5,645,549 A | 7/1997 | Boyd et al. |
| 5,667,509 A | 9/1997 | Westin |
| 5,667,513 A | 9/1997 | Torrie et al. |
| 5,681,320 A | 10/1997 | McGuire |
| 5,716,360 A | 2/1998 | Baldwin et al. |
| 5,720,753 A | 2/1998 | Sander et al. |
| 5,776,075 A | 7/1998 | Palmer |
| 5,817,109 A | 10/1998 | McGarry et al. |
| 5,820,630 A | 10/1998 | Lind |
| 5,843,108 A | 12/1998 | Samuels |
| 5,865,361 A | 2/1999 | Milliman et al. |
| 5,885,300 A | 3/1999 | Tokuhashi et al. |
| 5,891,150 A | 4/1999 | Chan |
| 6,004,332 A | 12/1999 | Yoon et al. |
| 6,022,356 A | 2/2000 | Noyes et al. |
| 6,024,708 A | 2/2000 | Bales et al. |
| 6,048,354 A | 4/2000 | Lawrence |
| 6,079,606 A | 6/2000 | Milliman et al. |
| 6,120,511 A | 9/2000 | Chan |
| 6,123,678 A | 9/2000 | Palmer |
| 6,129,683 A | 10/2000 | Sutton |
| 6,136,010 A | 10/2000 | Modesitt et al. |
| 6,200,322 B1 | 3/2001 | Branch et al. |
| 6,210,415 B1 | 4/2001 | Bester |
| 6,241,139 B1 | 6/2001 | Milliman et al. |
| 6,254,605 B1 | 7/2001 | Howell |
| 6,254,606 B1 | 7/2001 | Carney et al. |
| 6,267,763 B1 | 7/2001 | Castro |
| 6,330,965 B1 | 12/2001 | Milliman et al. |
| 6,342,057 B1 | 1/2002 | Brace et al. |
| 6,375,658 B1 | 4/2002 | Hangody et al. |
| 6,450,948 B1 | 9/2002 | Matsuura et al. |
| 6,491,645 B1 | 12/2002 | Gaber |
| 6,508,496 B1 | 1/2003 | Huang |
| 6,582,451 B1 | 6/2003 | Marucci |
| 6,656,205 B1 | 12/2003 | Manhes |
| 6,669,073 B2 | 12/2003 | Milliman et al. |
| 6,701,812 B1 | 3/2004 | Sawamura |
| 6,716,228 B2 | 4/2004 | Tal |
| 6,840,932 B2 | 1/2005 | Lang |
| 6,918,916 B2 | 7/2005 | Gobel et al. |
| 6,929,647 B2 | 8/2005 | Cohen |
| 6,953,139 B2 | 10/2005 | Milliman et al. |
| 6,964,668 B2 | 11/2005 | Modesitt et al. |
| 7,001,400 B1 | 2/2006 | Modesitt et al. |
| 7,090,680 B2 | 8/2006 | Bonati et al. |
| 7,112,208 B2 | 9/2006 | Morris et al. |
| 7,192,431 B2 | 3/2007 | Hangody et al. |
| 7,201,756 B2 | 4/2007 | Ross et al. |
| 7,204,839 B2 | 4/2007 | Dreyfuss et al. |
| 7,235,087 B2 | 6/2007 | Modesitt et al. |
| 7,264,622 B2 | 9/2007 | Michelson |
| 7,303,107 B2 | 12/2007 | Milliman et al. |
| 7,341,564 B2 | 3/2008 | Zwiefel |
| 7,341,596 B2 * | 3/2008 | Heppler ........... A61B 17/32093 606/167 |
| 7,351,201 B2 | 4/2008 | Ouchi |
| 7,422,594 B2 | 9/2008 | Zander |
| 7,481,824 B2 | 1/2009 | Boudreaux et al. |
| 7,488,327 B2 | 2/2009 | Rathbun et al. |
| 7,565,993 B2 | 7/2009 | Milliman et al. |
| 7,594,917 B2 | 9/2009 | Whittaker et al. |
| 7,624,902 B2 | 12/2009 | Marczyk et al. |
| 7,624,903 B2 | 12/2009 | Green et al. |
| 7,625,378 B2 | 12/2009 | Foley |
| 7,681,772 B2 | 3/2010 | Green et al. |
| 7,828,187 B2 | 11/2010 | Green et al. |
| 7,842,042 B2 | 11/2010 | Reay-Young |
| 7,871,422 B2 | 1/2011 | Shibata |
| 7,985,239 B2 | 7/2011 | Suzuki |
| 8,197,482 B2 | 6/2012 | Stone |
| 8,282,647 B2 | 10/2012 | Re |
| 8,317,862 B2 | 11/2012 | Troger et al. |
| 8,343,161 B2 | 1/2013 | Re |
| 8,523,872 B2 | 9/2013 | Ek |
| 8,617,168 B2 | 12/2013 | Bourque et al. |
| 8,685,033 B2 | 4/2014 | Johnson et al. |
| 8,690,885 B2 | 4/2014 | Smith |
| 8,771,273 B2 | 7/2014 | Homan et al. |
| 8,790,352 B2 | 7/2014 | Smith et al. |
| 8,840,615 B2 | 9/2014 | Bourque |
| 2001/0016746 A1 | 8/2001 | McGuire et al. |
| 2001/0053934 A1 | 12/2001 | Schmieding |
| 2002/0019649 A1 | 2/2002 | Sikora et al. |
| 2002/0117533 A1 | 8/2002 | Milliman et al. |
| 2002/0117534 A1 | 8/2002 | Green et al. |
| 2002/0133165 A1 | 9/2002 | Whittaker et al. |
| 2002/0143342 A1 | 10/2002 | Hangody et al. |
| 2002/0143354 A1 | 10/2002 | Lang |
| 2003/0009173 A1 | 1/2003 | McGuire et al. |
| 2003/0009218 A1 | 1/2003 | Boucher et al. |
| 2003/0083688 A1 | 5/2003 | Simonson |
| 2003/0083695 A1 | 5/2003 | Morris |
| 2003/0093093 A1 | 5/2003 | Modessitti et al. |

(56) References Cited

U.S. PATENT DOCUMENTS

| | | |
|---|---|---|
| 2003/0216742 A1 | 11/2003 | Wetzler et al. |
| 2004/0015170 A1 | 1/2004 | Tallarida et al. |
| 2004/0049195 A1 | 3/2004 | Singhatat et al. |
| 2004/0073227 A1 | 4/2004 | Dreyfuss et al. |
| 2004/0147932 A1 | 7/2004 | Burkinshaw et al. |
| 2004/0181246 A1 | 9/2004 | Heppler |
| 2004/0193172 A1 | 9/2004 | Ross et al. |
| 2004/0220588 A1 | 11/2004 | Kermode et al. |
| 2004/0267276 A1 | 12/2004 | Camino et al. |
| 2005/0027299 A1 | 2/2005 | Metzger |
| 2005/0033365 A1 | 2/2005 | Courage |
| 2005/0113841 A1 | 5/2005 | Sheldon |
| 2005/0149045 A1 | 7/2005 | Elliott |
| 2005/0165420 A1 | 7/2005 | Cha |
| 2005/0177179 A1 | 8/2005 | Baynham et al. |
| 2005/0222601 A1 | 10/2005 | Erhard |
| 2005/0228399 A1 | 10/2005 | Kubo et al. |
| 2005/0245924 A1 | 11/2005 | Tuke et al. |
| 2005/0245934 A1 | 11/2005 | Tuke |
| 2005/0261692 A1 | 11/2005 | Carrison et al. |
| 2006/0041263 A1 | 2/2006 | Chu et al. |
| 2006/0069394 A1 | 3/2006 | Weiler et al. |
| 2006/0085006 A1 | 4/2006 | Ek et al. |
| 2006/0106398 A1 | 5/2006 | Lauryssen et al. |
| 2006/0119014 A1 | 6/2006 | Towers et al. |
| 2006/0155290 A1 | 7/2006 | Shino |
| 2006/0195106 A1 | 8/2006 | Jones et al. |
| 2006/0195112 A1 | 8/2006 | Ek |
| 2006/0271059 A1 | 11/2006 | Reay-Young |
| 2007/0118136 A1 | 5/2007 | Ek |
| 2007/0152014 A1 | 7/2007 | Gillujm et al. |
| 2007/0179340 A1 | 8/2007 | Jorgenson |
| 2007/0191852 A1 | 8/2007 | Shimko et al. |
| 2007/0191853 A1 | 8/2007 | Stone |
| 2007/0233128 A1 | 10/2007 | Schmieding et al. |
| 2007/0233136 A1 | 10/2007 | Wozencroft |
| 2007/0233151 A1 | 10/2007 | Chudik |
| 2007/0233241 A1 | 10/2007 | Graf et al. |
| 2007/0244508 A1 | 10/2007 | Weizman |
| 2007/0270804 A1 | 11/2007 | Chudik |
| 2007/0276370 A1 | 11/2007 | Altarac et al. |
| 2007/0282356 A1 | 12/2007 | Remiszewski et al. |
| 2007/0282358 A1 | 12/2007 | Remiszewski et al. |
| 2008/0027435 A1 | 1/2008 | Zucherman et al. |
| 2008/0027457 A1 | 1/2008 | Dienst et al. |
| 2008/0097453 A1 | 4/2008 | Stone |
| 2008/0103506 A1 | 5/2008 | Volpi et al. |
| 2008/0140748 A1 | 6/2008 | Lada |
| 2008/0188859 A1 | 8/2008 | Reitzig et al. |
| 2008/0221581 A1 | 9/2008 | Shoham |
| 2008/0306485 A1 | 12/2008 | Coon et al. |
| 2008/0306487 A1 | 12/2008 | Hart |
| 2009/0018654 A1 | 1/2009 | Schmieding et al. |
| 2009/0048673 A1 | 2/2009 | Le Huec |
| 2009/0069845 A1 | 3/2009 | Frushell et al. |
| 2009/0076512 A1 | 3/2009 | Ammann et al. |
| 2009/0143784 A1 | 6/2009 | Petersen et al. |
| 2009/0157081 A1 | 6/2009 | Homan et al. |
| 2009/0157110 A1 | 6/2009 | Muto et al. |
| 2009/0163766 A1 | 6/2009 | Torrie |
| 2009/0163935 A1 | 6/2009 | McCarthy et al. |
| 2009/0171355 A1 | 7/2009 | Amis et al. |
| 2009/0171360 A1 | 7/2009 | Whelan |
| 2009/0216236 A1 | 8/2009 | Re |
| 2009/0216243 A1 | 8/2009 | Re |
| 2009/0222013 A1 | 9/2009 | Graf et al. |
| 2009/0228031 A1 | 9/2009 | Ritter et al. |
| 2009/0254093 A1 | 10/2009 | White |
| 2009/0281545 A1 | 11/2009 | Stubbs |
| 2010/0016984 A1 | 1/2010 | Trabish |
| 2010/0030029 A1 | 2/2010 | Markham |
| 2010/0030116 A1 | 2/2010 | Chana |
| 2010/0042106 A1 | 2/2010 | Bryant et al. |
| 2010/0049200 A1 | 2/2010 | Re |
| 2010/0049201 A1 | 2/2010 | Re |
| 2010/0057077 A1 | 3/2010 | Ducharme |
| 2010/0068233 A1 | 3/2010 | Bangera et al. |
| 2010/0121337 A1 | 5/2010 | Pandya |
| 2010/0137872 A1 | 6/2010 | Kam et al. |
| 2010/0137924 A1 | 6/2010 | Tuke |
| 2010/0249930 A1 | 9/2010 | Myers |
| 2010/0256645 A1 | 10/2010 | Zajac et al. |
| 2010/0268241 A1 | 10/2010 | Flom et al. |
| 2010/0292743 A1 | 11/2010 | Singhal |
| 2011/0087258 A1 | 4/2011 | Sluss |
| 2011/0251621 A1 | 10/2011 | Sluss |
| 2011/0282350 A1 | 11/2011 | Kowarsch et al. |
| 2011/0313478 A1 | 12/2011 | Herdrich et al. |
| 2012/0046526 A1 | 2/2012 | Boettner et al. |
| 2012/0059382 A1 | 3/2012 | Paulos |
| 2012/0059469 A1 | 3/2012 | Myers et al. |
| 2012/0109136 A1 | 5/2012 | Bourque et al. |
| 2012/0116402 A1 | 5/2012 | Schneider |
| 2012/0150301 A1 | 6/2012 | Gamache et al. |
| 2012/0197261 A1 | 8/2012 | Rocci et al. |
| 2013/0085494 A1 | 4/2013 | Weisenburgh et al. |
| 2014/0107657 A1 | 4/2014 | Norton et al. |
| 2014/0303635 A1 | 10/2014 | Smith et al. |

FOREIGN PATENT DOCUMENTS

| | | |
|---|---|---|
| CN | 201182625 Y | 1/2009 |
| CN | 201612662 U | 10/2010 |
| DE | 102007057075 A1 | 5/2009 |
| EP | 0643945 A2 | 3/1995 |
| EP | 1444959 A1 | 8/2004 |
| EP | 1882456 A | 1/2008 |
| EP | 1917921 A2 | 5/2008 |
| EP | 2311394 A1 | 4/2011 |
| FR | 2716364 A | 8/1995 |
| FR | 2906452 A1 | 4/2008 |
| FR | 2911264 A1 | 7/2008 |
| FR | 2918554 A1 | 1/2009 |
| GB | 2230453 A | 10/1990 |
| JP | H10-174689 | 6/1998 |
| JP | 2002102236 A | 4/2002 |
| JP | 2003531676 | 10/2003 |
| JP | 2005507697 A | 3/2005 |
| JP | 2009195705 | 9/2009 |
| JP | 2009261812 | 11/2009 |
| JP | 2010527705 | 8/2010 |
| JP | 2011507639 A | 3/2011 |
| JP | 2011520475 A | 7/2011 |
| JP | 201275604 | 4/2012 |
| RU | 2125844 C1 | 2/1999 |
| RU | 2241394 C2 | 12/2004 |
| RU | 46642 U1 | 7/2005 |
| WO | 8800458 A1 | 1/1988 |
| WO | 9929237 A1 | 6/1999 |
| WO | 9956628 | 11/1999 |
| WO | 0140748 A1 | 6/2001 |
| WO | 0236020 A1 | 5/2002 |
| WO | 2003037163 A2 | 5/2003 |
| WO | 2005037065 A2 | 4/2005 |
| WO | 2005037150 A1 | 4/2005 |
| WO | 2006088452 A2 | 8/2006 |
| WO | 2009082497 A1 | 7/2009 |
| WO | 2012103535 A1 | 8/2012 |
| WO | 2014107729 A2 | 7/2014 |

OTHER PUBLICATIONS

Office Action from related Mexican Patent Application No. MX/A/2013/003496 dated Sep. 29, 2016.

First Office Action for related Chinese Patent Application No. 201180046481 dated Feb. 15, 2015.

International Search Report and Written Opinion for PCT/US2011/053545 dated Dec. 19, 2011.

Communication of the Substantive Examination Report for related Mexico Patent Application No. MX/a/2013/003496 dated Oct. 20, 2015.

(56) References Cited

OTHER PUBLICATIONS

Shino, Konsei, "Triple Bundle ACL Reconstruction Using the Smith and Nephew ENDOBUTTON CL Fixation System" Knee Series. Technique Guide. Andover, Massachusetts: 2007.

Office Action from related Mexican Application No. MX/a/2013/003496 dated Jun. 6, 2017.

Communication from related EP Application No. 08729966.5-1659 dated Jul. 7, 2017.

Kayvani, K., "Analysis and Esign of Cable Supported Roof Structures," <https://books.google.com/books?d=xlgyl_U1lTkC&pg=PA59&lpg=PA59&dq=high+tensile+strangth+steel+characteristics+flexibility&source=bl&ots=I2WZYv2_LR&sig=wdmKuugAPuSRTQjyvuqJ7AKqutl&hl=en&sa=X&ei=Ke0eVYS4G8z3sAWPvYC4CA&ved=0CE4Q6AEwBw#v=one page&q&f=true> accessed May 14, 2015.

Matsuda, D.K.,"FAI: An emerging problem in orthopedics," Orthopedics Today, Jul. 2009, Retrieved from www.healio.com on Jan. 11, 2013.

\* cited by examiner

DEVICE AND METHODS FOR USE DURING ARTHROSCOPIC SURGERY

CROSS REFERENCE TO RELATED APPLICATIONS

This application is a divisional application of U.S. patent application Ser. No. 13/246,799, filed on Sep. 27, 2011 which claims priority to U.S. Patent Application Ser. No. 61/386,718, the disclosure of which is incorporated herein by reference in its entirety.

BACKGROUND

Field of Technology

The present disclosure relates generally to arthroscopic surgery and, specifically to a device and methods for use during arthroscopic surgery.

Related Art

During hip arthroscopy, it is often necessary for a surgeon to use an arthroscopy knife to make incisions that will allow the surgeon to gain access to areas near the hip joint. For example, the knife may be used to detach the labrum from the acetabular rim. During the same procedure, the knife may be used to make an incision in the hip capsule. Using the knife to detach the labrum from the acetabulum has its drawbacks because the point at which the knife will exit the labrum is not known prior to making the cut. Therefore, a knife and specifically, methods of use that allow for more precision control of the knife are needed.

SUMMARY

In one aspect, the present disclosure relates to a method of use during arthroscopic surgery. The method includes inserting a cannulated needle into a joint area of the body, inserting a guidewire through the needle, removing the needle, and inserting an arthroscopy knife into the joint area via the use of the guidewire.

In an embodiment, the method further includes using the knife to detach a portion of the soft tissue from the bone, performing surgery on the bone, and reattaching the detached portion of the soft tissue to the bone. In another embodiment, the knife includes a proximal end and a distal end. In yet another embodiment, the distal end includes a blade and a guidewire component. In a further embodiment, the soft tissue is a labrum and the bone is an acetabulum. In yet a further embodiment, the step of inserting an arthroscopy knife into the joint area via use of the guidewire includes coupling the arthroscopy knife to the guidewire and inserting the knife into the joint area such that a blade of the knife is inserted between the soft tissue and bone. In yet an even further embodiment, coupling the arthroscopy knife to the guidewire includes inserting the guidewire through the component. In an embodiment, the method further comprises using the knife to make an incision in the hip.

In another aspect, the present disclosure relates to an arthroscopy knife. The knife includes a proximal end and a distal end, the distal end including a blade and a guidewire component.

In an embodiment, the distal end is curved. In another embodiment, the guidewire component includes a through hole.

In yet another aspect, the present disclosure relates to a method of use during arthroscopic surgery. The method includes inserting a cannulated needle through a first passage into a joint area of the body; inserting a guidewire through the needle; inserting an arthroscopy knife into the joint area via the use of the guidewire; and creating an incision in a capsule surrounding the joint, the incision located between the first passage and a second passage.

In an embodiment, the method further includes removing the needle after inserting the guidewire. In another embodiment, the method further includes using the knife to detach a portion of soft tissue from bone, performing surgery on the bone, and reattaching the detached portion of the soft tissue to the bone. In yet another embodiment, the knife includes a proximal end and a distal end. In a further embodiment, the distal end includes a blade and a guidewire component. In yet a further embodiment, the soft tissue is a labrum and the bone is an acetabulum. In yet a further embodiment, the step of inserting an arthroscopy knife into the joint area via use of the guidewire includes coupling the arthroscopy knife to the guidewire and inserting the knife into the joint area such that a blade of the knife is inserted between the soft tissue and bone. In an embodiment, coupling the arthroscopy knife to the guidewire includes inserting the guidewire through the component.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION OF THE EMBODIMENTS

The following description of the preferred embodiment(s) is merely exemplary in nature and is in no way intended to limit the disclosure, its application, or uses.

Figures 1, 1A:
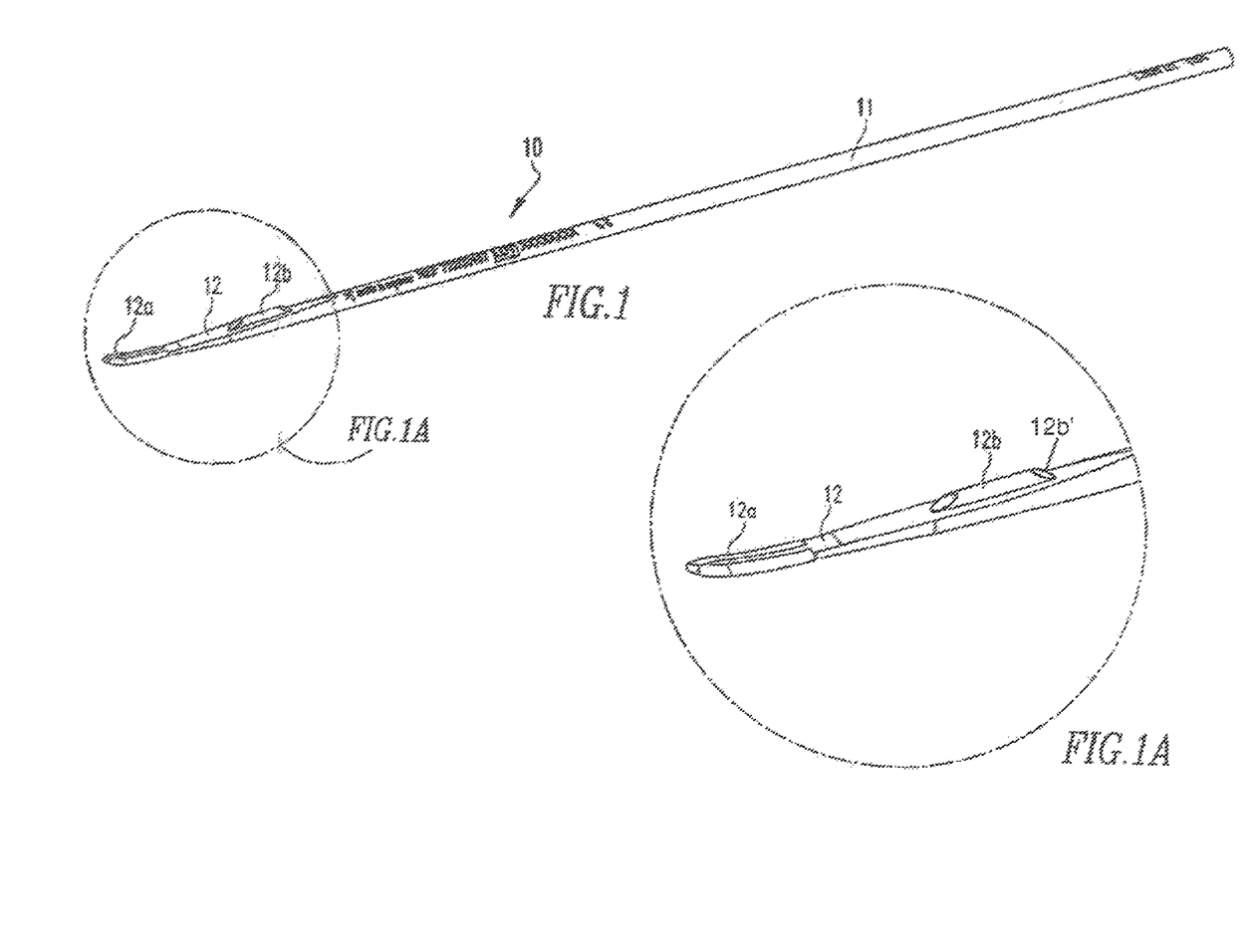
FIG. 1 shows a perspective view of the arthroscopy knife of the present disclosure.
FIG. 1A shows an exploded view a distal end of the knife of FIG. 1.

As shown in FIGS. 1 and 1A, the knife 10 includes a proximal end 11 and a distal end 12. The proximal end 11 is configured for being held by a user, such as a surgeon. The distal end 12 includes a blade 12a and a guidewire component 12b, the purpose of which will be further described below. The distal end 12, especially the blade 12a, may be curved, as shown in FIGS. 1 and 1A. Having a curved distal end 12 biases the blade 12a against a guidewire when the blade 12a is coupled to a guidewire, as is further shown in FIGS. 2A-2E and described below, which minimizes the amount of divergence between the blade 12a and the guidewire. However, a knife 10 having a non-curved distal end may also be used.

Figure 2A:
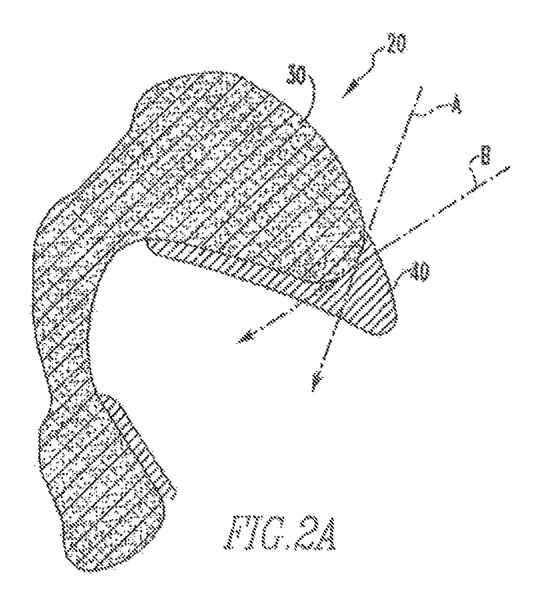
FIGS. 2A-2E show a method of detaching a soft tissue from bone during arthroscopic surgery.
Figure 2B:
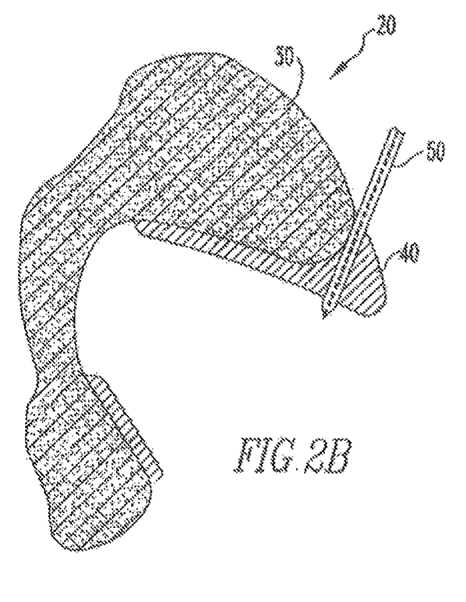
Figure 2C:
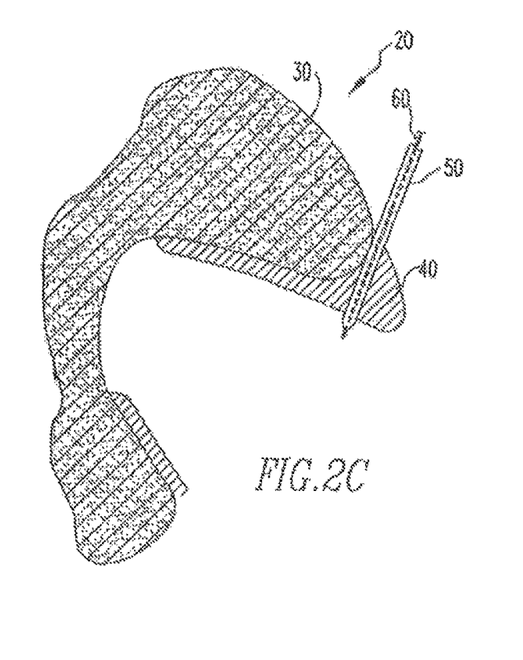
Figure 2D:
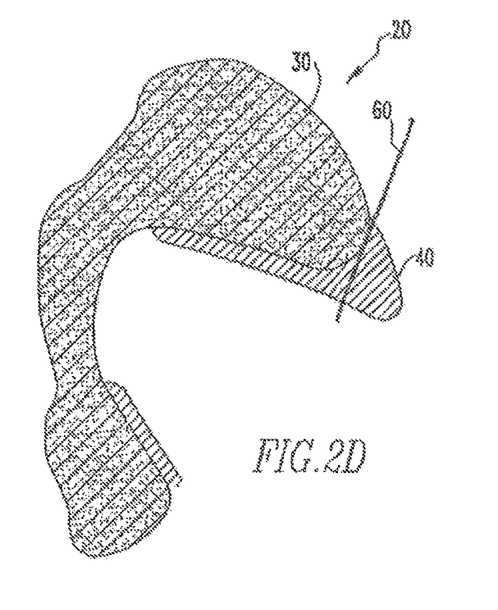
Figure 2E:
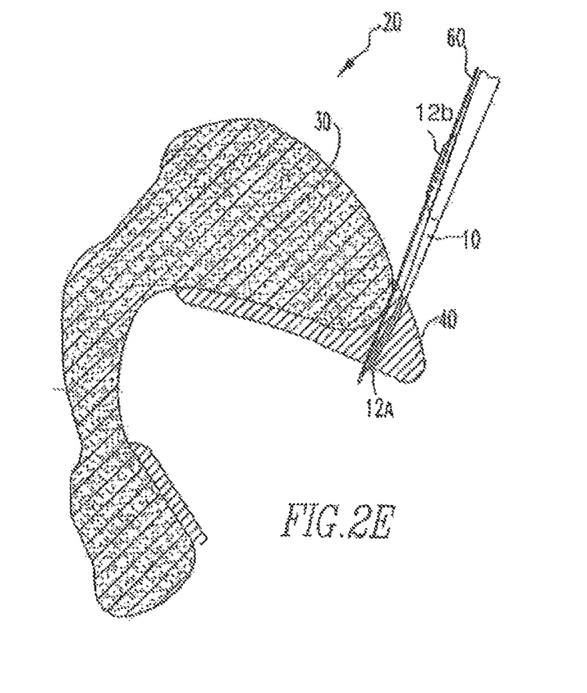

As mentioned above, one of the uses for the knife 10 is detaching soft tissue from bone. Specifically, the knife 10 is used in surgery on the hip joint 20 to detach a labrum 40 from an acetabulum 30, as shown in FIGS. 2A-2E, A cannulated needle 50 is disposed within the joint 20 along one of the trajectories A,B, as shown in FIGS. 2A-2B. Other trajectories may be used. A guidewire 60 is then disposed through the cannulation of the needle 50 and the needle 50 is removed from the joint, as shown in FIGS. 2C and 2D. Subsequently, the knife 10 is inserted into the joint 20 via use of the guidewire 60. Specifically, the knife 10 is coupled to the guidewire 60 by inserting the guidewire 60 through the through hole 12b' of the component component 12b and sliding the knife 10 along the guidewire 60 and into the joint 20, such that the blade 12a is located between the acetabulum 30 and the labrum 40, as shown in FIG. 2F. The surgeon operates the knife 10 to cut at least a portion of the labrum 40 away from the acetabulum 30, the purpose of which is to allow access to a portion or portions of the acetabulum 30 where surgery is needed. Subsequently, the knife 10 is removed and surgery on the acetabulum 30 is performed. Once surgery is completed, the detached portion of the labrum 40 is reattached to the acetabulum 30 via the use of soft tissue anchors or other fixation devices known to those of skill in the art.

Figure 3:
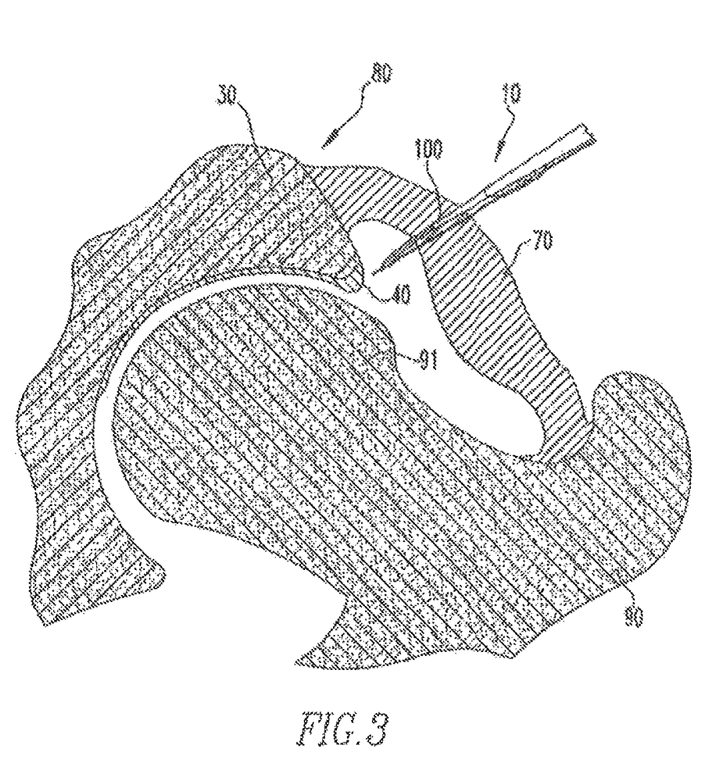
FIG. 3 shows a cross-sectional view of the hip joint while an incision is being made in the hip capsule.

FIG. 3 shows the use of the knife 10 in creating an incision in the hip capsule 70. The capsule 70 is a thick layer of soft tissue surrounding the joint 80, ie the area where the head 91 of the femur 90 is inserted into the acetabulum 30. This thick layer makes changing the trajectory of instruments placed into the joint 80 difficult. For instance, a first instrument (not shown), such as an endoscope, and a second instrument, such as the knife 10, may both be inserted through the capsule 70 and into the joint 80 via the use of separate portals or passages. In order to make the use of these instruments less difficult, an incision or slit may be made in the capsule 70 that would connect the portals and allow for less restricted movement of the instruments. This method of creating an incision in the hip capsule 70 may be used in conjunction with the above-described method of detaching soft tissue from bone. For instance, prior to cutting a portion of the labrum 40 away from the acetabulum 30, the knife 10 may be inserted into the joint area 80, as described above, and then used to create the incision between the knife portal 100 and the endoscope portal.

For purposes of clarity, FIG. 3 only shows a cross-sectional view of the hip joint 80 and the knife passage 100. While the endoscope passage is usually placed within close proximity to the knife passage 100, the endoscope passage may be created anywhere along the capsule 70 that would allow the surgeon to view the surgical area. The passage 100 may also be used for other instruments, such as an anchor delivery device, or other devices used in surgery on the hip joint 80.

For the purposes of this disclosure, the arthroscopy knife 10 is made from a metal material. However, other materials could be used. The knife 10 is made via a process known to one of skill in the art. Additionally, the knife may be used in either manner described above in a joint area other than the hip joint. Furthermore, the incision made in the capsule may be made in other manners. For example, the incision does not have to connect the portals.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. An arthroscopy knife comprising:
   a proximal end and a distal end, the distal end including a blade, and
   a guidewire component by which the knife is couplable to a guidewire wherein the guidewire component defines a longitudinal axis for receiving the guidewire,
   wherein the longitudinal axis of the guidewire component intersects with the blade when the knife is not coupled to the guidewire and the blade is in an unbiased state,
   whereby the guidewire component is configured to bias the blade against the guidewire when the knife is coupled to the guidewire via the guidewire component and the blade is touched to the guidewire.

2. The arthroscopy knife of claim 1 wherein the blade is curved towards the longitudinal axis of the guidewire component so as to intersect with the longitudinal axis of the guidewire component when the knife is not coupled to the guidewire and the blade is in an unbiased state.

3. The arthroscopy knife of claim 1 wherein the guidewire component is an elongated tubular member defining a through hole for receiving the guidewire.

4. The arthroscopy knife of claim 1 wherein the knife includes a shaft extending between the proximal end and the distal end, and wherein the guidewire component is mounted directly to the shaft.

5. The arthroscopy knife of claim 4 wherein a distal region of the shaft is tapered along the longitudinal axis of the knife toward the distal end.

6. The arthroscopy knife of claim 5 wherein the guidewire component is mounted to a tapered surface of the shaft which angles the guidewire component relative to the shaft.

7. The arthroscopy knife of claim 1, wherein the longitudinal axis of the guidewire component intersects with a portion of the blade proximal to a distal tip when the knife is not coupled to the guidewire and the blade is in an unbiased state.

8. The arthroscopy knife of claim 7, wherein the guidewire component is configured to bias the blade against the guidewire when the knife is coupled to the guidewire via the guidewire component and the distal tip of the blade is touched to the guidewire.

9. The arthroscopy knife of claim 1, wherein the blade is distally positioned relative to the guidewire component.

10. An arthroscopy knife comprising:
    a proximal end and a distal end, the distal end including a blade, and
    a guidewire component by which the knife is couplable to a guidewire wherein the guidewire component defines a longitudinal axis for receiving the guidewire,
    whereby the guidewire component is configured to bias the blade against the guidewire when the knife is coupled to the guidewire via the guidewire component and the blade is touched to the guidewire, and
    wherein the blade is curved towards the longitudinal axis of the guidewire component so as to intersect with the longitudinal axis of the guidewire component when the knife is not coupled to the guidewire and the blade is in an unbiased state.

11. The arthroscopy knife of claim 10, wherein the guidewire component is an elongated tubular member defining a through hole for receiving the guidewire.

12. The arthroscopy knife of claim 10, wherein the knife includes a shaft extending between the proximal end and the distal end, wherein the guidewire component is mounted directly to the shaft.

13. The arthroscopy knife of claim 12, wherein a distal region of the shaft is tapered along a longitudinal axis of the knife toward the distal end.

14. The arthroscopy knife of claim 13, wherein the guidewire component is mounted to a tapered surface of the shaft which angles the guidewire component relative to the shaft.

15. The arthroscopy knife of claim 10, wherein the blade is distally positioned relative to the guidewire component.

16. The arthroscopy knife of claim 10, wherein a distal tip of the blade is touched to the guidewire.

17. An arthroscopy system comprising:
a guidewire, and
an arthroscopy knife including:
   a proximal end and a distal end, the distal end including a blade, and
   a guidewire component, proximal to the blade, by which the knife is couplable to the guidewire wherein the guidewire component defines a longitudinal axis for receiving the guidewire,
wherein the guidewire component is configured such that when the arthroscopy knife is coupled to the guidewire via the guidewire component and the blade is touched to the guidewire, the guidewire component biases the blade against the guidewire, and
wherein the longitudinal axis of the guidewire component intersects with the blade when the knife is not coupled to the guidewire and the blade is in an unbiased state.

18. The system of claim 17, wherein the longitudinal axis of the guidewire component intersects with a portion of the blade proximal to a distal tip when the knife is not coupled to the guidewire and the blade is in an unbiased state.

* * * * *